(12) United States Patent
Laurent et al.

(10) Patent No.: US 12,264,312 B2
(45) Date of Patent: Apr. 1, 2025

(54) METHOD FOR EXTRACTING NUCLEIC ACIDS

(71) Applicant: BIOMÉRIEUX, Marcy L'Etoile (FR)

(72) Inventors: Alain Laurent, Grenoble (FR); Arnaud Burr, Saint Martin Le Vinoux (FR); Ali Laayoun, La Frette (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 1056 days.

(21) Appl. No.: 16/979,565

(22) PCT Filed: Mar. 15, 2019

(86) PCT No.: PCT/FR2019/050591
§ 371 (c)(1),
(2) Date: Sep. 10, 2020

(87) PCT Pub. No.: WO2019/175518
PCT Pub. Date: Sep. 19, 2019

(65) Prior Publication Data
US 2021/0009989 A1    Jan. 14, 2021

(30) Foreign Application Priority Data
Mar. 16, 2018   (FR) ........................ 1852257

(51) Int. Cl.
*C12N 15/10*    (2006.01)
(52) U.S. Cl.
CPC ................ *C12N 15/1006* (2013.01)
(58) Field of Classification Search
None
See application file for complete search history.

(56) References Cited

U.S. PATENT DOCUMENTS

| 6,248,570 B1 | 6/2001 | Michon et al. |
| 7,244,568 B2 | 7/2007 | Goldsborough |
| 2002/0082416 A1 | 6/2002 | Park et al. |
| 2011/0065906 A1* | 3/2011 | Liu .................... C12N 1/06 |
| | | 435/325 |
| 2017/0269069 A1 | 9/2017 | An et al. |

FOREIGN PATENT DOCUMENTS

| JP | 2004-057064 A | 2/2004 |
| WO | 00/75302 A2 | 12/2000 |
| WO | 2003/68788 A1 | 8/2003 |
| WO | 2004/013155 A2 | 2/2004 |

OTHER PUBLICATIONS

Boom et al., J Clin Microbiol., Mar. 1990; 28(3): 495-503. (Year: 1990).*
Jun. 25, 2019 International Search Report issued in International Patent Application No. PCT/FR2019/050591.
Qiagen. "Qiaquick Spin Handbook". Sep. 1, 2018, <URL: https://www.qiagen.com/us/resources/resourcedetail?id=ebad21f3-1d09-4c1f-b823-76dfd601eb82&lang=en> [retrieved on Nov. 9, 2018].
Christian A.G.N. Montalbetti et al. "Amide Bond Formation and Peptide Coupling". Tetrahedron, Elsevier Science Publishers, vol. 61, No. 46, Nov. 14, 2005, pp. 10827-10852.

* cited by examiner

*Primary Examiner* — Nicole Kinsey White
(74) *Attorney, Agent, or Firm* — Oliff PLC

(57) ABSTRACT

A method for extracting nucleic acids using suitable solid supports, for example silica-based. In particular, the method includes a step of capturing nucleic acids by placing the sample in contact with a suitable solid support, characterized in that, prior to the capture step, said method includes a step of treating the sample with at least one reagent for masking the amine or carboxylic acid functional groups of the proteins and/or polysaccharides of the sample.

19 Claims, 9 Drawing Sheets

METHOD FOR EXTRACTING NUCLEIC ACIDS

The present invention relates to a method for extracting nucleic acids using a suitable solid support, for example silica-based. In particular, the method comprises a step of capturing nucleic acids by placing the sample in contact with a suitable solid support, characterized in that said method comprises, prior to the capturing step, a step of treating the sample with at least one reagent in order to mask the amine and/or carboxylic acid functional groups of the proteins and/or polysaccharides of the sample.

PRIOR ART

The rise of molecular biology has led to huge advances in diagnosis. From a test sample, it is possible to extract and detect nucleic acids belonging to the host or to infectious microorganisms contained in the sample. The detection or even the quantification of this genetic material makes it possible to establish a diagnosis concerning a microbial infection or the presence of oncogenes. This is usually done in three steps as described below:

1) The extraction of nucleic acids from complex biological samples (blood, tumor, food, etc.), which consists of a chemical or mechanical lysis of the cells in order to release their contents and in particular the nucleic acids. These are then selectively purified and subsequently amplified if their quantity is insufficient for direct detection.

2) The amplification of purified nucleic acids by DNA amplification techniques: NASBA, RT-PCR, PCR, etc. This step is necessary when the amount of nucleic acids collected from a biological sample is very low or the test is not sensitive enough for direct detection.

3) The detection of amplified nucleic acids by techniques known as endpoint, real-time, sequencing, etc. Depending on the detection technique used, this step may enable selective quantification of the target nucleic acids being tested for.

For a sensitive and specific detection of nucleic acids, and in particular in order to make a diagnosis as accurate as possible, it appears essential to extract and/or isolate the nucleic acids (DNA and RNA) from the cells in an efficient manner. This extraction and/or purification step is generally critical, because this first step will dictate the quality of the series of events leading to the final result of the diagnostic test. It is therefore necessary to have a nucleic acid extraction that is as specific and effective (in quantity, purity, and time) as possible, so as not to lose information which can lead to a misdiagnosis and can be fatal for a patient.

Many techniques have been developed for attempting to extract nucleic acids from different biological samples. The oldest methods involve a multitude of steps generally consisting of enriching the cells containing the nucleic acids, lysing these cells, separating and removing the proteins, membranes, and other cellular components, and purifying the remaining nucleic acids by precipitation in organic solvents. These techniques are expensive, time-consuming, and often impossible to automate. They are therefore no longer suitable for current practices where automation is necessary in order to obtain results quickly and avoid problems of contamination and of human error, particularly in cases of sepsis "blood infection" where patient survival is threatened.

The more recent nucleic acid extraction techniques use solid phases where the cells are lysed under specific reaction conditions and the released nucleic acids bind to the solid phase. It is well known in the state of the art that current nucleic acid extraction techniques very often make use of solid phases which are, for example, particles coated with silica. Silica has the property of reversibly adsorbing nucleic acids under certain conditions of salt concentration and pH, making it a very suitable material for this purpose. These techniques are described for example in "Rapid and simple method for purification of nucleic acids," Boom, Journal of Clinical Microbiology, 1990 p. 495 or in U.S. Pat. No. 5,234,809 by the same author.

It is also known to use magnetic particles coated with silica. The magnetic portion of the particles is most often used to facilitate and automate the steps of capturing, washing, and eluting the nucleic acids because a simple magnet enables the displacement of particles in the tube and the collection of supernatants for washing steps. The extraction yields of the nucleic acids are significantly improved. These techniques are well described in "*Magnetic Partials for the Separation and Purification of Nucleic Acids*", S. Berensmeier, Applied Microbial Biotechnology 2006 73 495-504; "*The use of magnetic nanoparticles in the development of new molecular detection systems*", I. J. Bruce, Journal of Nanosciences and Nanotechnology (2006), 6 (8) pp. 2302-2311; and "*Optimization of influencing factors of nucleic acid adsorption onto silica-coated magnetic particles: Application to viral nucleic acid extraction from serum*", Ning Sun et al., Journal of Chromatography A, 2014, 1325, 31-39.

The present disclosure aims to provide methods for extracting nucleic acids that meet one or more of the following criteria:
1) Simplicity of implementation,
2) Possible implementation on different sources of biological samples,
3) Implementation of the method in an essentially aqueous medium,
4) Good extraction yield,
5) High purity level of the nucleic acid after extraction,
6) Possibility of automation,
7) DNA of sufficient quality for a step of amplification and/or detection of a sequence of interest, particularly in the context of an in vitro diagnostic test, and/or
8) Better detection sensitivity with a more reliable result.

SUMMARY

The present disclosure relates to a method for extracting nucleic acids from a sample comprising proteins and/or polysaccharides, said method comprising a step of capturing nucleic acids by placing the sample in contact with a suitable solid support, characterized in that, prior to the capture step, said method comprises a step of treating the sample with at least one reagent for masking the amine and/or carboxylic acid functional groups of the proteins and/or polysaccharides of the sample. In one specific embodiment, the reagent for masking the amine functional groups is selected from acylating or alkylating agents. For example, the masking reagent is selected from the acylating agents of the following formula (I):

where R is an organyl, organyloxy, or organylamino group

LG is a leaving group selected from the group consisting of halogens, organyloxy and organylamino groups.

More specifically, the masking reagent may be an acylating agent selected from the group consisting of activated esters, acid halides, chloroformates, anhydrides, activated carbonate esters, and carbonyldiimidazole. In another embodiment, the masking reagent is an anhydride selected from acetic anhydride, propionic anhydride, isobutyric anhydride, butyric anhydride, or benzoic anhydride.

In another embodiment, the masking reagent is an alkylating agent selected from the group consisting of alkyl halides, diazo compounds, and aldehydes.

In another embodiment, the masking reagent is selected from amines, alcohols, and thiols for the masking of the carboxylic acid functional groups of the proteins, in combination with a coupling agent. We can cite the carbodiimides as examples of coupling agents, for example 1-ethyl-3-(3-dimethylaminopropyl) carbodiimide (EDC), diisopropylcarbodiimide (DIC), or dicyclohexylcarbodiimide (DCC).

In one particular embodiment, which may be combined with the above embodiments, the method for extracting nucleic acids from a biological sample comprises the following steps:

a. lysing the cells, for example by placing the biological sample in contact with a lysis buffer,
b. treating the lysate with the reagent for masking the amine and/or carboxylic acid functional groups of the proteins and/or polysaccharides of the sample,
c. capturing the nucleic acids by placing the treated lysate in contact with a suitable solid support, for example a silica-based support,
d. where appropriate, washing the support with a wash buffer, and
e. where appropriate, eluting the nucleic acids.

Typically, in the method defined above, the solid support may consist of silica particles, in particular magnetic silica particles.

In one particular embodiment, which may be combined with the above embodiments, the biological sample is a sample of blood, plasma, or serum.

In one particular embodiment, which may be combined with the above embodiments, the capture step is carried out in the presence of chaotropic agents.

In one particular embodiment, which may be combined with the above embodiments, the extraction method does not comprise the use of proteases for the removal of proteins.

In one particular embodiment, which may be combined with the above embodiments, no organic solvent is added before or during the nucleic acid capture step. Advantageously, less than 50 µL of organic solvent is added, preferably less than 10 µL, and even more preferably less than 1 µL, before or during the nucleic acid capture step, per 100 µL of sample.

In one particular embodiment, which may be combined with the above embodiments, the method comprises an additional step of detecting nucleic acids of interest, in particular by amplification of the extracted nucleic acids.

The present disclosure also relates to nucleic acid extraction kits comprising at least:

i. a reagent for masking the amine and/or carboxylic acid functional groups of the proteins and/or polysaccharides as defined above,
ii. a suitable solid support, for example silica-based, for the extraction of the nucleic acids,
iii. where appropriate, a catalyst for the reaction of masking the amine and/or carboxylic acid functional groups using the reagent,
iv. where appropriate, a coupling agent.

The present disclosure also relates to the use of a reagent for masking the amine and/or carboxylic acid functional groups of the proteins and/or polysaccharides as defined above, for nuclease inhibition. For example, the nuclease to be inhibited is comprised in a lysate obtained by lysis of a biological sample, for example for the purposes of amplification or detection of a nucleic acid in the sample.

Definitions

"Extraction" is understood to mean a technique for isolating nucleic acids from any sample, for example isolation of DNA and/or RNA from eukaryotic cells, prokaryotic cells, human animal cells, cells of microorganisms or of tissue. Extraction from a biological sample in the meaning of the invention thus generally includes lysis of the cells and purification of nucleic acids from the lysate.

The purification itself comprises the capture of nucleic acids on a suitable solid support, preferably silica-based, and washing, possibly followed by elution of the nucleic acids. The capture consists of adsorbing the nucleic acids on the solid support, and the elution, when it takes place, consists of their desorption or release from the solid support.

"Sample" is understood to mean any type of sample comprising at least nucleic acids and agents inhibiting the extraction of nucleic acids, such as proteins and/or polysaccharides. The sample may have various origins such as samples of dietary, environmental, human, veterinary, or cosmetic origins. All these samples, if they are not liquid, are pretreated to be in liquid form. The sample used in the extraction process is therefore in liquid form. Preferably, the sample used in the extraction process is an unfixed sample. "Unfixed sample" is understood to mean a sample that has not been processed so as to be preserved in its original state. Fixation of a sample is a technique well-known to those skilled in the art, which may for example be carried out with an aldehyde such as formaldehyde or glutaraldehyde.

Examples of samples of dietary origin include, but are not limited to, a sample of milk products (yogurts, cheeses, etc.), of meat, fish, eggs, fruits, vegetables, beverages (milk, fruit juice, soda, etc.). Of course, these samples of dietary origin may also come from sauces or more elaborate dishes or from unprocessed or partially processed raw materials. A dietary sample may also come from feed intended for animals, such as feed cakes, meat and bone meal.

As indicated above, the sample may be of environmental origin and may consist, for example, of surface sampling, water sampling, etc.

The sample may also consist of a biological sample of human or animal origin, which may correspond to samples from biological fluid (urine, whole blood or derivatives such as serum or plasma, sputum or saliva, pus, cerebrospinal fluid, etc.), from stools (for example cholera diarrhea), samples from the nose, throat, skin, wounds, organs, isolated tissues or cells, swab specimens, bronchoalveolar lavages or specimens, biopsies. This list is obviously not exhaustive.

The term "sample" generally refers to a portion or quantity, more particularly a small portion or a small quantity, collected for analysis from one or more entities. This sample may possibly have undergone prior treatment, involving for example steps of mixing, dilution, or crushing, particularly if the initial entity is in the solid state.

In general, the analyzed sample is likely to contain—or suspected of containing—at least some nucleic acids representative of the presence of microorganisms, of a patient's condition (for example immunosuppression, pregnancy, etc.) or of a disease to be detected, characterized, or monitored.

In one particular embodiment, the sample comprises proteins having an isoelectric point of less than 8, or even less than 7. In particular, in one particularly specific embodiment, the sample comprises at least one of the following proteins: human serum albumin (HSA), fibrinogen, immunoglobulins especially IgG, and hemoglobin.

"Microorganism" is understood to mean some or all of a bacterium, a fungus, a yeast, a protozoan, or a virus.

"Nucleic acids" is understood to mean DNA or RNA of all types: genomic DNA, complementary DNA, messenger RNA, complementary RNA, transfer RNA, mitochondrial RNA, chloroplast DNA, ribosomal RNA, plasmid DNA, viral DNA or RNA, microRNA, snoRNA, siRNA, RNAi, in single-stranded or double-stranded form.

"Proteins" is understood to mean any molecule comprising at least one polypeptide chain, characterized by a sequence of amino acid residues linked together by peptide bonds. This includes, in particular, the peptides and polypeptides and any modified polypeptide or its derivatives resulting from post-translational or other modifications, their degradation products especially by enzymatic degradation, the lipoproteins, etc.

"Suitable solid support" is understood to mean any support capable of participating in the extraction of nucleic acids from a biological sample. In one preferred embodiment, it is a support comprising or consisting of silica or one of its derivatives (silicate, glass, silica modified with organic groups, etc.), magnetic or non-magnetic, and capable of participating in the extraction of nucleic acids from a biological sample. It may also be a support based on paper, cellulose, or pure magnetite, or other polymers known for their uses in the extraction of nucleic acids. It may be at least a flat support, a hollow support, a wafer, a needle, a membrane, a plate, a sheet, a cone, a tube, fibers, a bead, a particle, etc. The solid support is preferably a bead or particle or membrane. The solid support is preferably magnetic.

In one embodiment of the method for extracting nucleic acids from a biological sample, the method comprises the following steps:
a) lysing the cells, for example by placing the biological sample in contact with a lysis buffer,
b) treating the lysate with a reagent for masking the amine and/or carboxylic acid functional groups of the proteins and/or polysaccharides of the lysate,
c) capturing the nucleic acids by placing the treated lysate in contact with a suitable solid support,
d) where appropriate, washing the support with a wash buffer and eluting the nucleic acids.

Advantageously, step b) is directly followed by step c), in other words there is no intermediate step between steps b) and c), for example no step of deprotecting the masked functional groups. In one specific embodiment, the method for extracting nucleic acids does not comprise a step of deprotecting the masked amine and/or carboxylic acid functional groups.

The present disclosure also relates to the use of a reagent for masking the amine and/or carboxylic acid functional groups of the proteins and/or polysaccharides in a method for extracting nucleic acids from a biological sample using a suitable solid support.

The steps of this method are described in more detail below.

Lysis Step

The lysis step involves rupturing the sample cells (cell walls and membranes) in order to release the nucleic acids. There are several methods of lysis: in particular we can cite mechanical (for example with beads and/or an abrasive material), chemical, or enzymatic lysis, or lysis by thermal shock.

In one specific embodiment, the cells are chemically lysed by placing the sample in contact with a lysis buffer. The lysis buffer must be effective in rupturing the cell membranes as well as gentle enough not to degrade the nucleic acids.

The lysis buffer may comprise, for example, a detergent and where appropriate a chelating agent. The pH is generally maintained between 4 and 8, for example between 6 and 8, using a suitable buffer, for example Tris HCl, optionally in concentrations of between 10 and 100 mM.

The detergent may be selected among Tween, Triton, SDS, and other detergents commonly used at concentrations between 0.05 and 20%.

Optionally, the lysis buffer contains reagents for inactivation of the nucleases, and/or for removal of proteins, for example proteases such as proteinase K. Other enzymes may also be used such as lytic enzymes (hydrolase, zymolase, etc.) to digest the wall of yeasts and fungi.

In one specific embodiment, the lysis buffer does not comprise reagents for the removal of proteins and in particular proteases. Indeed, the inventors have shown that the reagent for masking the amine and/or carboxylic functional groups used in the extraction method according to the present disclosure advantageously also allows inhibition of the enzyme activity of nucleases that may have been released into the lysate.

In one specific embodiment, the lysis buffer also comprises chaotropic agents. Chaotropic agents interfere with weak (non-covalent) intramolecular interactions, such as hydrogen bonds, van der Waals forces, and hydrophobic forces. Among the chaotropic agents, we can cite urea, guanidine salts such as guanidinium chloride or thiocyanate, and lithium perchlorate. They are generally used in concentrations ranging from 1 to 6 M, particularly for GuSCN and GuHCl.

In another specific embodiment, the lysis buffer does not comprise chaotropic agents.

Chelating agents may also be added, such as EDTA or similar compounds, for example between 5 and 50 mM, and/or reducing compounds such as DTT (dithiothreitol) or TCEP (tris carboxyethyl phosphine) or beta-mercaptoethanol at concentrations, for example, of between 0.5 and 100 mM.

The lysis buffer may also comprise organic solvents such as alcohols (ethanol, isopropanol, etc.). In a preferred embodiment, however, the lysis buffer does not comprise organic solvents.

The chemical characteristics of a sample must be taken into account when optimizing the lysis buffer. For example, the acidity of a sample (e.g. some soil samples) can damage nucleic acids and therefore may be neutralized to ensure a decent yield of nucleic acids. The sample is placed in contact with the lysis buffer for sufficient time to allow lysis of the cells without damaging the nucleic acids, for example between 0 and 15 min.

Treating the Sample or Lysate with Masking Reagent

An essential characteristic of the method for extracting nucleic acids according to the present disclosure concerns the step of treating the lysate with a reagent for masking the amine and/or carboxylic acid functional groups of the proteins and/or polysaccharides of the sample. This treatment step may be carried out by adding the masking reagent to the lysate, after the lysis step. Alternatively, the masking reagent is included directly in the lysis buffer, the lysis and treatment of the sample occurring concurrently. The goal is to neutralize the charged functional groups of the proteins and/or polysaccharides likely to affect the yield from extraction by means of a solid support, preferably silica-based. Indeed, in the following examples, the inventors have demonstrated the impact of biomolecules on the extraction yield, and in particular proteins and/or polysaccharides of biological samples in extraction methods using solid supports such as silica-coated particles. The proteins and/or polysaccharides may in particular interact with the silica beads and/or the nucleic acids via their charged functional groups, and in particular their amine and/or carboxylic acid functional groups.

The inventors then had the idea of using reagents for masking these charged functional groups, and in particular the amine and/or carboxylic acid functional groups of the proteins and/or polysaccharides, in order to block this inhibitory effect of biomolecules. "Masking reagent" is therefore understood to mean any chemical compound capable of reacting (preferably irreversibly) with at least certain amine and/or carboxylic acid functional groups of the proteins and/or polysaccharides present in a lysate of a biological sample, so as to change the properties of polarity, isoelectric point, and/or charge of these proteins and/or polysaccharides. Treatment with the masking reagent makes it possible to mask the charged functional groups, and especially the amine and/or carboxylic acid functional groups of the proteins and/or polysaccharides. However, in one specific embodiment, the nucleic acids are not modified by the masking reagent. The reaction conditions, and in particular the concentration of masking reagent, can be chosen so that the nucleic acids are not modified during the masking step. In one specific embodiment, the concentration of masking reagent or of coupling agent, when it is present, is between 0.01 M and 1.8 M, for example between 0.1 M and 1.0 M, for example between 0.2 and 0.6 M.

In one specific embodiment, the masked amine and/or carboxylic acid functional groups of the modified proteins and/or polysaccharides remain masked throughout the duration of the method for extracting nucleic acids according to the present disclosure. In this case, the method for extracting nucleic acids does not comprise a step of deprotecting the masked amine and/or carboxylic acid functional groups.

In one specific embodiment, the masking reagent is chosen from acylating or alkylating agents, making it possible to mask the amine functional groups of the proteins or polysaccharides. Preferably, the acylating or alkylating agent must be able to mask the amine functional groups of the proteins or polysaccharides in an aqueous medium.

Typically, an acylating agent that can be used as a masking reagent in the method for extracting nucleic acids has the following formula (I):

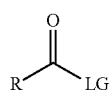

(I)

where
R is an organyl, organyloxy, or organylamino group;
LG is a leaving group.

"Leaving group" is understood to mean an atom or a group which, during the acylation reaction, detaches from the carbon atom to which it is bound.

In one embodiment, LG is a leaving group selected from the group consisting of halogens, organyloxy and organylamino groups.

In one particular embodiment, the masking reagent may be an acylating agent selected from the group consisting of activated esters, acid halides, chloroformates, anhydrides, activated carbonate esters, and carbonyldiimidazole. Among the activated esters, mention may be made of tetra or pentafluorophenyl acetate, nitrophenyl acetate, pentafluorophenyl trifluoroacetate, and N-hydroxysuccinimide esters such as N-hydroxysuccinimide acetate. Among the acid halides, mention may be made of acid chlorides such as the chloride of acetic acid, of propionic acid, of isobutyric acid, of butyric acid, or of benzoic acid. Among the chloroformates, mention may be made of 9-fluorenylmethyl chloroformate (Fmoc-Cl). Among the anhydrides, mention may be made of acetic, propionic, isobutyric, butyric, benzoic, maleic, succinic or phthalic anhydride. Among the activated carbonate esters, mention may be made of di-tert-butyl dicarbonate ($Boc_2O$).

In a particularly preferred embodiment, the masking reagent is acetic anhydride or its dry form, N-hydroxysuccinimide acetate.

In another specific embodiment, an alkylating agent may be selected from the group consisting of alkyl halides, aryl sulfates, aryl diazomethyls, triazenes, and aldehydes. Among the alkyl halides, mention may be made of methyl, ethyl, or propyl iodide, or methyl bromide. Among the aryl diazomethyl compounds, mention may be made of methyl diazopyridine (WO2010012949A1). Among the aldehydes, mention may be made of formaldehyde and acetaldehyde.

In one embodiment, the acylating or alkylating reagent is used in combination with a catalyst known to those skilled in the art. In the case of acylation with acetic anhydride, 4-dimethylaminopyridine (DMAP) for example can be used as a catalyst.

In another embodiment, the reagent used is selected from amines, alcohols, and thiols, for the masking of the carboxylic acid functional groups of the proteins and/or polysaccharides, in combination with a coupling agent. The coupling agent is used to activate the carboxylic acid functional groups of the proteins and/or polysaccharides by forming activated esters. These activated esters will then react with a nucleophile selected from amines, alcohols, and thiols. The nucleophile may be present on the protein and/or polysaccharide (amine, alcohol, or thiol of an amino acid of the protein and/or polysaccharide) or in the medium, as in the case of a nucleophilic buffer, for example Tris.

The coupling agent may for example be selected from the carbodiimides, among which we can cite 1-ethyl-3-(3-dimethylaminopropyl) carbodiimide (EDC), diisopropylcarbodiimide (DIC), and dicyclohexylcarbodiimide (DCC). The carbodiimides may be used in combination with other reagents such as N-hydroxysuccinimide and the triazoles, among which we can cite 1-hydroxybenzotriazole (HOBt) and 1-hydroxy-7-azabenzotriazole (HOAt).

The masking reagent may also be bi-functionalized or multifunctionalized in order to establish bridges between the reactive residues of the proteins (bridging compounds such as bis-aldehyde, bis-N-hydroxysuccinimide ester, bis-acid chloride, and their derivatives).

For example, an acylating agent such as acetic anhydride may be used in concentrations between 0.01 M and 1.8 M, for example between 0.1 M and 1.0 M, for example between 0.2 and 0.6 M. The concentration of the masking reagent used for treating the sample may be adjusted according to the concentration of proteins and/or polysaccharides in the sample, the masking reagent used, the source of the sample, and the lysis conditions used. The concentration of acylating agent may be chosen so as to react with the amine and/or carboxylic acid functional groups of the proteins and/or polysaccharides, without reacting with the nucleic acids.

The incubation time of the lysate, or the sample being lysed when the lysis and treatment step are concurrent, in the presence of the masking reagent is generally between 1 second and 30 minutes, but preferably less than 10 minutes.

In one embodiment, a step of controlling the acidity of the treated lysate is performed, for example with sodium hydroxide (NaOH), in particular in order to obtain a pH of the treated lysate that is preferably between 5 and 7. The amount of sodium hydroxide added during this step is low, this step therefore only making it possible to control the pH before the capture step, it not being a step of deprotecting the masked amine and/or carboxylic acid functional groups of the proteins and/or polysaccharides. This step of controlling the acidity of the treated lysate is optional; in one particular embodiment, this step is not present.

At the end of the treatment step, a treated lysate is obtained comprising modified proteins and/or polysaccharides. In particular, at least a portion of the amine and/or carboxylic acid functional groups of the proteins and/or polysaccharides is masked after treatment; preferably the nucleic acids are not modified by the masking reagent.

Capture

The capture step consists of placing the treated lysate in the presence of a solid support, for example a silica-based solid support, under conditions permitting the adsorption of the nucleic acids (solid-phase extraction of the nucleic acids). The silica-based support, for example silica beads or particles, makes it possible to separate the nucleic acids, retained by adsorption on the silica, from other cellular contaminants (membranes, proteins treated with the masking reagent, etc.). Advantageously, no antibody is used during the capture step.

In one specific embodiment, the capture step takes place directly after the step of treating the sample or lysate with the masking reagent. In this case, there is no intermediate step between the masking step and the capture step. In particular, there is no step of deprotecting the masked amine and/or carboxylic acid functional groups between the masking step and the capture step, or during the capture step. Preferably, during the capture step, the sample comprises modified proteins and/or polysaccharides (i.e. masked by the masking reagent) and unmodified nucleic acids (i.e. not masked by the masking reagent).

In one specific embodiment, a sufficient amount of silica beads or particles is added to the treated lysate. In this embodiment with silica beads, preferably the conditions enabling the adsorption of nucleic acids include the presence of chaotropic agents, such as guanidinium chloride or guanidinium thiocyanate in a buffered medium between pH 4 and pH 8, for example with the aid of organic compounds such as TRIS (Tris(hydroxyethyl) aminomethane) salts, salts of acetate, of phosphate, of citrate, or of MES (morpholino ethanesulfonic acid).

It is also possible to add a detergent, preferably Triton X100 or one of its analogs (Tergitol, Tween, Brij, Nonidet, Ecosurf, etc.). In another embodiment, said detergent is contained in the lysis buffer. The silica-based support is preferably negatively charged, between pH 5.0 and pH 8.0.

In one particular embodiment, chaotropic agents or alcohols are not used during the step of capture by adsorption on the solid support. A suitable support will then be used, in particular an amino support.

As examples of silica beads or particles that are usable for the capture step, we can cite the particles included in the following kits: NucliSENS easyMAG Magnetic Silica (BioMerieux), Film Array (BioMérieux/Biofire Diagnostic), Qiasymphony kits (Qiagen), and Magnapure Kits (Roche).

In another embodiment, the silica-based solid support is an extraction column with a silica membrane. As examples, we can cite the kits sold under the names Purelink Genomic DNA Extraction Kit (Invitrogen), and DNeasy Blood and Tissue Kit (Quiagen). The treated lysate is deposited on the column with silica membrane, then centrifuged so that the lysate passes through the column. The nucleic acids are retained on the column and the proteins, polysaccharides, and other cellular debris pass through the column.

Other silica-based supports and their uses for the extraction of nucleic acids are described in particular in the following articles: Cady et al., Nucleic acid purification using micro fabricated silicon structures. Biosensors and Bioelectronics 19, 59-66 (2003); A. Melzak, C. S. Sherwood, R. F. B. Tumer, C. A. Haynes, Driving Forces for DNA Adsorption to Silica in Perchlorate Solutions. J Colloid and Interface Science 181, 635-64 (1996); Tian et al., Evaluation of Silica Resins for Direct and Efficient Extraction of DNA from Complex Biological Matrices in a Miniaturized Format, Analytical Biochemistry 283, 175-191 (2000); Wolfe et al., Toward a microchip-based solid-phase extraction method for isolation of nucleic acids. Electrophoresis 23, 727-733 (2002).

In another embodiment, magnetic silica particles are used. The magnetic silica particles can be retained by a magnet during the steps of washing, and where appropriate elution, following capture. This embodiment is particularly preferred for automation of the extraction process. Examples of usable magnetic particles include the kit sold under the name NucliSENS easyMAG Magnetic Silica (BioMérieux).

In one particular embodiment, the method for extracting nucleic acids from an unfixed sample comprising proteins and/or polysaccharides comprises a step of capturing the nucleic acids by placing the unfixed sample in contact with a suitable solid support, characterized in that, prior to the capture step, said method comprises a step of treating the sample with at least one reagent in order to mask the amine and/or carboxylic acid functional groups of the proteins and/or polysaccharides of the sample, and in that the capture step takes place directly after the step of treating the sample with the masking reagent.

Washing and Elution

After the capture step, one or more washing steps may be carried out in the presence of a wash buffer, enabling the removal of contaminating elements without detaching the nucleic acids from the support. The washing step may for example comprise a step of washing in a suitable wash buffer, for example a low-salt solution possibly containing an alcohol, and/or a step of washing in the presence of an alcohol in order to eliminate salts. In a preferred embodiment of the invention, at least one washing step is performed.

If necessary, an elution step may then be performed. The elution step consists of releasing the nucleic acids retained on the solid support. In general, a buffer is used of basic pH, for example a pH of between 8 and 10, and of low ionic strength, such as Tris or borate buffer. Alternatively, one proceeds directly to the detection or amplification step after the capture and washing steps. This detection and/or amplification is carried out directly on the suitable solid support that has captured the purified nucleic acids, with no prior elution step. Preferably, this is done on a bead or a particle or a membrane and more preferably on a particle that may or may not be magnetic.

The nucleic acids thus purified by the method described above (with or without an elution step) may be used in particular for applications of amplification and detection in vitro.

Additional Steps of Amplification and/or Detection

The invention is particularly suitable for the preparation of nucleic acids for the purpose of detecting nucleic acids of interest in a sample (in vitro detection test), in particular after amplification of a nucleic acid of interest.

The invention therefore relates to a method for detecting a nucleic acid sequence of interest in a biological sample, said method comprising:
(i) extracting the nucleic acids from a biological sample likely to contain a nucleic acid sequence of interest,
(ii) detecting the nucleic acid sequence in the extracted nucleic acids.

According to one particular embodiment, the detection step (ii) comprises a step of amplifying the nucleic acid sequence of interest.

Therefore, the invention also relates to a method for amplifying a nucleic acid, comprising: (i) implementing a method for extracting nucleic acid on a suitable support as described above, and (ii) a nucleic acid amplification step using a DNA polymerase.

One of the advantages of the present method is that the amplification step can take place just after the capture step. Since the nucleic acids are not modified by the masking reagent, it is not necessary to deprotect them before proceeding with the amplification.

In one specific embodiment, the amplification method is carried out using a DNA polymerase, such as Taq polymerase, Pfu polymerase, T7 polymerase, the Klenow fragment of E. coli DNA polymerase and/or a reverse transcriptase, or any other polymerase.

In another embodiment that can be combined with the preceding one, the amplification method is a polymerase chain reaction (PCR) amplification, well known to those skilled in the art. The PCR protocol comprises 20 to 40 cycles for example, each cycle comprising at least (i) a phase of denaturing the DNA to be amplified at a temperature generally between 90° C. and 95° C., (ii) a phase of hybridizing the primers with the DNA to be amplified at a temperature generally between 55° C. and 65° C., and (iii) an extension phase at a temperature generally between 68° C. and 75° C.

Variants of nucleic amplification methods by PCR may also be implemented. In particular, we can cite Nested PCR, quantitative PCR (or qPCR), semi-quantitative or real-time PCR, error-prone PCR, or reverse transcription PCR (RT-PCR). It is also possible to implement other amplification techniques such as LAMP, NASBA, TMA, RPA, LCR, RCR, 3SR, RCA, SDA, or any nucleic acid amplification techniques known to those skilled in the art.

Nucleic Acid Extraction Kits

The invention also relates to nucleic acid extraction kits or sets comprising at least:
i. a reagent for masking the amine and/or carboxylic acid functional groups of the proteins and/or polysaccharides as described in the preceding paragraphs, for example an acylating agent and preferably acetic anhydride or its dry form, N-hydroxysuccinimide acetate,
ii. a solid support suitable for the extraction of nucleic acids,
iii. where appropriate, a catalyst for the reaction of masking the amine and/or carboxylic acid functional groups using the reagent, and/or
iv. where appropriate, a coupling agent.

The extraction kit may further comprise buffers, controls, and/or instructions for use.

In one specific embodiment, the extraction kit does not comprise a reagent for deprotecting the masked amine and/or carboxylic acid functional groups.

In one specific embodiment, the extraction kit does not comprise an organic solvent.

In another particular embodiment, the kit may comprise the following elements:
i. a coupling agent, for example EDC,
ii. a suitable solid support, silica-based, for the extraction of nucleic acids, for example silica beads and in particular magnetic silica beads, and at least one of the following optional elements:
iii. a lysis buffer comprising Tris or another nucleophilic buffer,
iv. one or more wash buffers, and/or,
v. optionally, an elution buffer,
vi. optionally, a catalyst.

In one particular embodiment, the kit comprises a column with a silica membrane as a silica-based solid support.

These kits are useful in particular for implementing the extraction method as described in the preceding paragraphs. The method according to the present disclosure will be better understood with the aid of the examples detailed below and with reference to the appended figures.

EXAMPLES

General Conditions

Figure 1:
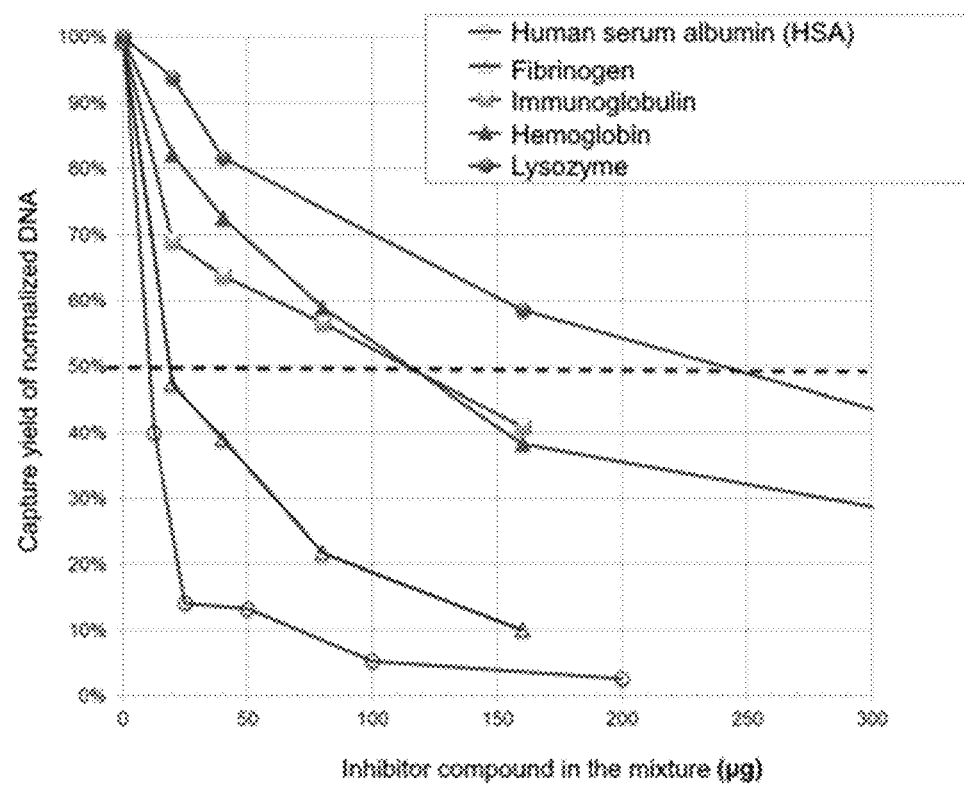
FIG. 1: Inhibition of DNA capture on a solid support by certain proteins under chaotropic conditions

The general conditions for the analysis of the compounds used in the following examples are described below:

The LC-MS analyses were carried out with a WATERS Alliance 2795 HPLC system equipped with a PDA 996 photodiode array detector (Waters), a ZQ 2000 mass spectrometry detector (Waters), and Empower software version 2. The ZQ 2000 mass spectrometer has an Electrospray ionization source. The ionizations were carried out in positive mode with a cone voltage of 20V and a capillary voltage of 3.5 kV.

The conditions used for the HPLC analyses were as follows (conditions A and B):

| Conditions | Eluent A<br>Eluent B<br>Eluent C | Linear<br>gradient |
|---|---|---|
| A | A: Milli-Q water<br>B: ACN<br>C: Ammonium<br>formate 500 mM, pH 7 | 98%/0%/2% -> 93%/5%/2% in<br>4 min -> 93%/5%/2% in 1 min -><br>86%/12%/2% in 5 min -><br>86%/12%/2% in 9 min -><br>8%/90%/2% in 1 min -><br>98%/0%/2% in 3 min Waters<br>XTerra MS reversed-phase<br>C18 column (2.5 µm,<br>4.6 × 300 mm), 30° C., flow<br>rate 1 ml/min, detection at 260 nm |
| B | A: Milli-Q water<br>B: ACN<br>C: TFA 500 mM, pH 1 | 78%/20%/2% -> 26%/72%/2% in<br>31 min -> 3%/95%/2% in<br>9 min -> 78%/20%/2% in 20<br>min Waters XBridge C4 column<br>(3.5 µm, 4.6 × 150 mm),<br>30° C., flow rate 1 ml/min,<br>detection at 260 nm |

Example 1a: Demonstration of the Inhibitory Effect of Protein Compounds from Blood for the Capture of Nucleic Acids on a Solid Support (Magnetic Silica Particles Used at pH 7)

To attempt to improve the performance of the extraction of nucleic acids on a silica-based solid support, the inventors have assumed that the first step is to attempt to increase the performance of the capture step.

To demonstrate the inhibitory effect of the compounds most represented in blood on the extraction of nucleic acids in the capture step, a solution of 200 µl containing 23 µg nucleic acids (salmon sperm DNA 20 Kb) in 4M GuHCl, 50 mM Tris pH 7 was prepared.

Increasing amounts of protein were added to this mixture (between 0 and 300 µg) to simulate a cellular lysate under chaotropic conditions as occurs under nucleic acid extraction conditions.

For each experiment, magnetic silica particles (50 µl at 20 mg/ml in water, 1 mg, easyMAG, bioMérieux, Marcy-l'Étoile, France) were added, and after stirring for 3 minutes the residual amount of DNA was measured by UV spectrometry at 260 nm. Knowing the amount of nucleic acid introduced and the amount adsorbed, it is then easy to calculate the amount of DNA adsorbed on the particles and thus the capture yield. A negative control was carried out each time on the solution of DNA and proteins. The curves are normalized relative to the reference without inhibitors.

It can be seen in FIG. 1 that the DNA capture is drastically reduced as soon as a few µg of proteins are added, until it is completely inhibited in the case of a hundred µg of HSA (Human Serum Albumin) for example.

The inhibitory effect seems to be partly related to the isoelectric point of the proteins; respectively in their order of inhibition, with human serum albumin (HSA) having an isoelectric point of 4.8, fibrinogen of 5.8, hemoglobin and immunoglobulin of 7, and lysozyme of 11.3. The more acidic the biomolecules, the more they compete with the capture of DNA. However, it should be noted that although the acid groups are the most competitive, the amine groups are also (see Example 2 for more on this subject).

This example thus demonstrates the inhibitory effect of compounds from blood on the extraction yield of nucleic acids, and more particularly the protein compounds that are negatively and positively charged. One can see that the most competitive compounds are those present in large quantities in blood (human serum albumin, fibrinogen, immunoglobulins, and hemoglobin).

Example 1b: Demonstration of the Inhibitory Effect of Polysaccharide Compounds for the Capture of Nucleic Acids on a Solid Support (Magnetic Silica Particles Used at pH 7)

Figure 2:
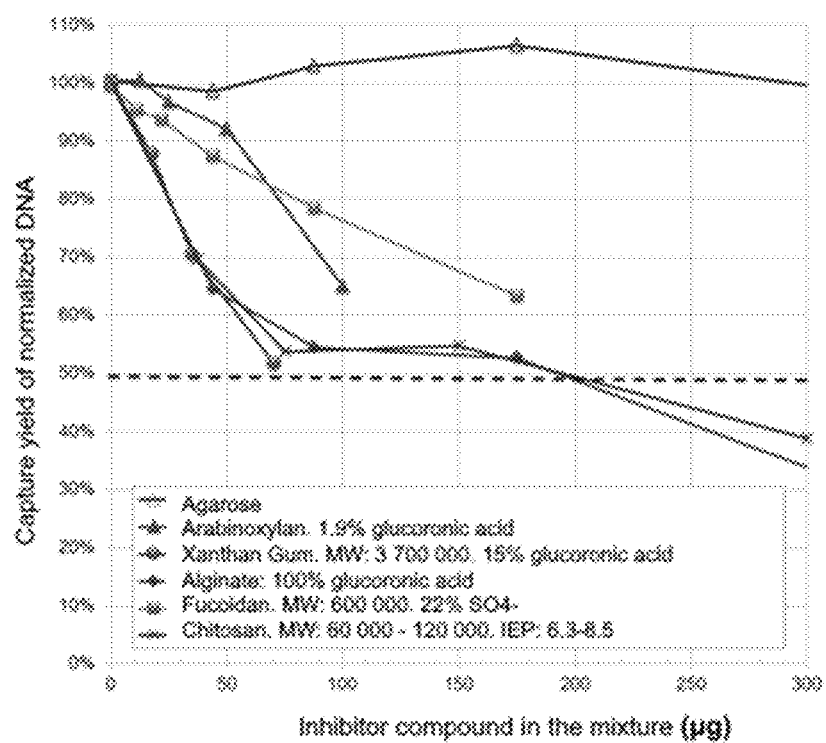
FIG. 2: Inhibition of DNA capture on a solid support by certain polysaccharides under chaotropic conditions

The experiment of Example 1a was carried out with other compounds such as either positively or negatively charged polysaccharides in place of the proteins. Here again, an inhibitory effect of the polysaccharides on the extraction yield of nucleic acids (see FIG. 2) is demonstrated.

Figure 3:
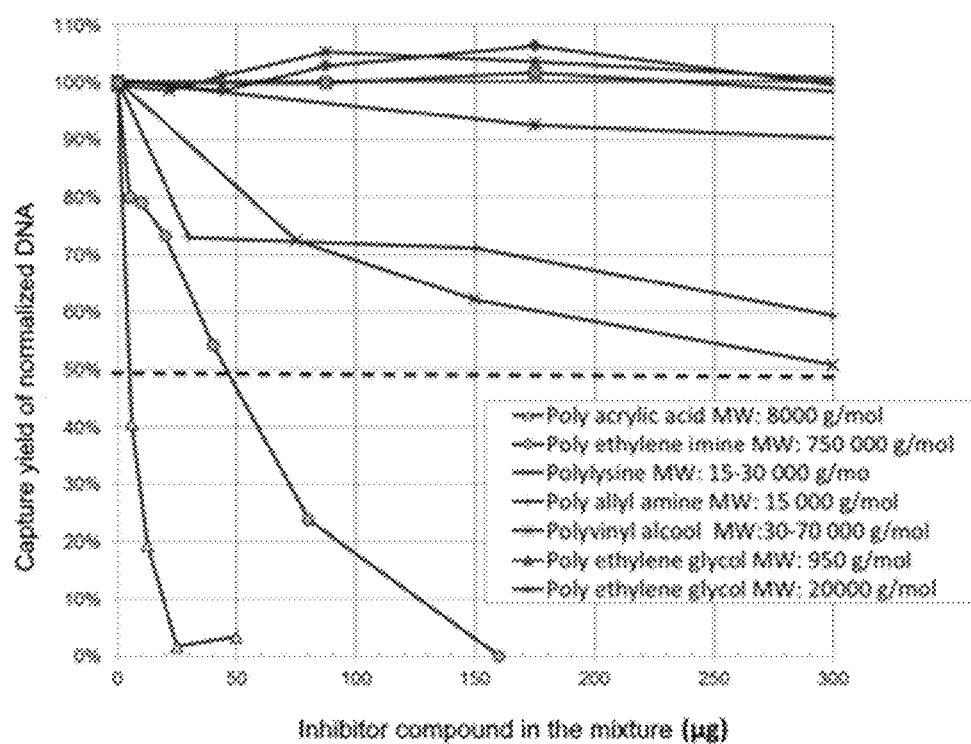
FIG. 3: Inhibition of DNA capture on a solid support by model mono-functional polymers.

Example 2: Role of the Charge and Chemical Composition of the Proteins on the Inhibition of the Capture of Nucleic Acids on a Solid Support In order to better understand the phenomenon of inhibition of the capture of nucleic acids on a solid support, the same experiment as the one described in Example 1 was carried out but using model compounds of polycarboxylic acids, polyamines, or polyalcohols instead of the corresponding proteins (FIG. 3). One can see very clearly that polycarboxylic acids are more inhibitory than polyamines, which in turn are much more inhibiting than polyalcohols or neutral compounds.

It requires about 10 µg of these compounds to inhibit the capture of DNA by 50%. This is consistent with what was previously observed with proteins in Example 1 or with polysaccharides in Example 1b.

The inhibitory effect of the amine and carboxylic acid functional groups of proteins and polysaccharides on the capture of nucleic acids in a biological sample is therefore definitely very pronounced: For example, a blood sample could contain between 200 and 500 mg/ml of proteins. Thus, under the actual conditions of nucleic acid extraction from 200 ml of blood, the sample could comprise at least 40 to 100 mg of compounds "inhibiting" the capture of nucleic acids.

Example 3: Inhibitory Effect of High Protein Concentration on Nucleic Acid Extraction, DNA Elution Yield, and Purity of the Extracted DNA (Magnetic Silica Particles Used at pH 7)

Although the competing effect of the proteins is already conspicuously negative under the conditions of the previous example, these conditions are far below the quantity of proteins that would actually be provided by 200 µl of blood (approximately 50 mg). In order to draw closer to reality, the inventors carried out another experiment where, this time, the equivalent of 5 mg protein (mixture of immunoglobulin, HAS, and hemoglobin in a concentration similar to what can be found in an actual blood sample) is or is not added to the 200 µl lysis solution.

The lysis solution respectively corresponds to 23 µg DNA in 200 µl GuHCl or GuSCN 3M, 50 mM Tris pH 7, 1% Triton X100, or easyMAG lysis buffer (bioMérieux, Marcy-l'Étoile, France) diluted to 3M.

To these solutions, 1 mg magnetic silica particles (easyMAG, bioMérieux, Marcy-l'Étoile, France) are added. The total DNA extraction yield is measured by UV spectrophotometric determination at 260 nm of the nucleic acids contained in the eluate, i.e. after capture on the magnetic silica particles, washing the particles with the easyMAG "Wash buffer 2" wash reagent, and eluting with the easyMAG "Elution buffer 3" elution reagent at 70° C. for 5 min.

TABLE 1

Extraction yield of 23 µg DNA in the presence or absence of protein inhibitors. Numbers in parentheses indicate the 260/280 nm ratio of the eluate.

| | Total extraction yield (capture and elution, %) (ratio 260/280) | | |
|---|---|---|---|
| | 3M GuHCl + Triton | 3M GuHSCN + Triton | 3M Lysis Buffer eMAG |
| DNA (23 µg) | 58% (2) | 62% (2) | 56% (2) |
| DNA (23 µg) + protein mixture (5000 µg) | 1% (1.2) | 4% (1.6) | 6% (1.6) |

As in the previous examples, a sharp drop in the extraction yield is observed. Regardless of the lysis conditions, the DNA extraction yield (capture, washing, elution) drops from about 60% to less than 6% when proteins are added to the medium.

The purity of the extracted nucleic acids is also greatly affected, because the presence of proteins lowers the 260/280 ratio representative of protein contamination in the final eluate, from 2 to less than 1.6 on average (see Table 1). This therefore reflects a very high protein concentration in the eluate.

This experiment clearly demonstrates that the protein compounds, and in particular the protein compounds of blood, used at a concentration similar to that found in a standard extraction, have a very strong impact on the capture of nucleic acids, due to the competitive effect. As a result, the overall extraction yield and the purity of the nucleic acids are affected.

Example 4: Increasing the DNA Extraction Yield by Using a Reagent for Masking the Amine and/or Carboxylic Acid Functional Groups in the Presence of a High Concentration of Proteins (Use of Magnetic Particles at pH 7)

The inventors carried out the same experiment as described in Example 3 above, this time adding a treatment with acetic anhydride or EDC prior to contact with the magnetic silica particles.

To do so, 23 µg DNA (10 µl DNA at 2.3 g/l) are incubated with 5000 µg proteins (25 µl of a mixture containing 150 g/l Hb, 50 g/l HAS, and 3 g/l fibrinogen in 50 mM Tris-HCl pH7 in concentrations similar to what could be found in an actual blood sample) in a solution of 200 µl GuHCl or GuSCN, 50 mM Tris pH 7, 1% Triton X100, or easyMAG lysis buffer at concentrations such as are found during extraction at 3M of chaotropic salts.

Sufficient acetic anhydride or EDC is added to reach 0.3M in the solution.

This is allowed to react for 5 min, neutralized with a few µl of 10 M sodium hydroxide to restore a pH of 7 (in the case of acetic anhydride only), and 1 mg magnetic silica particles are added which are incubated while stirring for 15 min before washing and eluting the purified nucleic acids as described in Example 3.

The total extraction yield is calculated relative to the initial 23 µg DNA and the amount of nucleic acids obtained in the eluate. The assay is performed by UV spectrophotometry at 260 nm.

It was shown in Table 2 that the presence of proteins during extraction considerably reduces the DNA extraction yield as well as its 260/280 nm ratio (from 60% to 5% and from 2 to 1.6 approximately, regardless of the conditions). However, preincubation of the lysate with acetic anhydride or EDC (respectively Ac2O or EDC in Table 2 below), prior to adding the magnetic silica particles, significantly restores the DNA extraction performance both in quantity (about 20%) and in purity (about 1.8).

This demonstrates the beneficial effect of prior protein masking on DNA extraction via a solid support under conditions similar to those found in a typical protocol for extracting nucleic acids.

In general, GuHSCN, which has a higher denaturing power than GuHCl, allows a better DNA capture yield in the presence of proteins. However, the presence of EDTA in the LB decreases the 260/280 ratio, while the Triton X-100 also present in the LB has a very beneficial effect.

TABLE 2

Extraction yield of 23 μg DNA in the presence or absence of protein inhibitors and with or without acetic anhydride (Ac2O) or EDC, and under different lysis conditions. Numbers in parentheses indicate the 260/280 nm ratio of the eluate.

| | Total extraction yield (capture and elution, %) (ratio 260/280) | | | | |
|---|---|---|---|---|---|
| | 3M GuHCl | 3M GuHCl + Triton | 3M GuHSCN | 3M GuHSCN + Triton | 3M Lysis Buffer eMAG |
| DNA (23 μg) | 54% | 58% (2) | 62% | 62% (2) | 56% (2) |
| DNA (23 μg) + protein mixture (5000 μg) | 0.8% (1.08) | 1% (1.2) | 2% (1.2) | 4% (1.6) | 6% (1.6) |
| DNA (23 μg) + protein mixture (5000 μg) + Ac2O (0.3M) | 20% (1.7) | 23% (1.7) | 9% (1.4) | 23% (1.9) | 15% (1.9) |
| DNA (23 μg) + protein mixture (5000 μg) + EDC (0.3M) | 24% (1.5) | ND | 22% (1.7) | ND | ND |

Example 5: Improving the Extraction Yield of Nucleic Acids in Blood (Extraction with Magnetic Particles at pH 7)

In order to demonstrate the beneficial effects of protein masking by a reagent, with an actual biological sample, we extracted the nucleic acids from 200 μl of blood by using magnetic silica particles (bioMérieux) and a slightly modified protocol using 3M GuHCl, 50 mM Tris HCl pH 7, 1% Triton for the lysis step, 50 mM Tris HCl pH 7 in 50% ethanol for the washes, and EasyMAG EB3 buffer (bioMérieux) for the final elution.

During the lysis step, the blood sample was subjected to treatment with 0.3M acetic anhydride or 0.3M acetic acid for 5 min, before being neutralized by the addition of a few μl of sodium hydroxide (in comparison to an untreated reference sample).

Following this treatment, the magnetic particles were added and the lysate placed in the easyMAG while following the extraction protocol of the supplier (bioMérieux). The amount of nucleic acids present in the blood was measured by UV spectrophotometry (Nanodrop, Thermofischer). It is noteworthy that the protocol using the masking reagent also works for a blood sample: Under the conditions used, the absence of treatment with acetic anhydride results in only 0.7 μg nucleic acids (0.9 purity) while the treatment with acetic anhydride results in more than 5 μg nucleic acids (for a purity greater than 1.9). In the control experiment, treatment with acetic acid demonstrates no improvement, which shows that the effect of acetic anhydride is related to its acylating power. Indeed, acetic acid is not an acylating agent and cannot mask the reactive functional groups of proteins.

There may be a large number of compounds co-extracted with the nucleic acids, which could distort the 260/280 ratio. In order to eliminate the errors inherent in using UV spectrophotometry to measure the optical density of an eluate resulting from extraction from a biological sample, we subjected these eluates to a complete hydrolysis with Nuclease P1 and alkaline phosphatase.

Figure 4A:
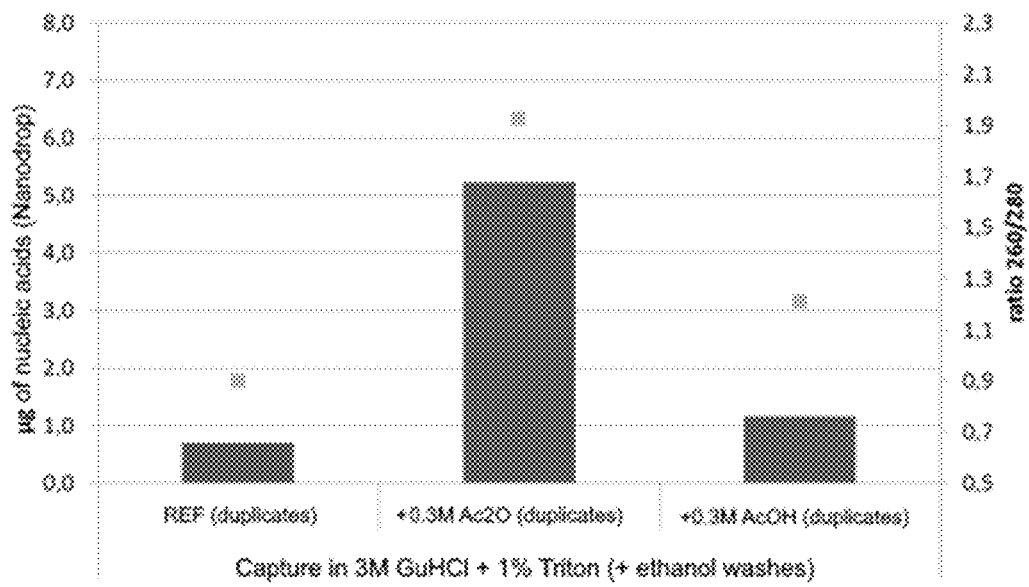
FIG. 4: A. Extraction of nucleic acids contained in a blood sample using the easyMAG extraction kit (BioMérieux) and pretreatment of the lysate with acetic anhydride (Ac2O) or acetic acid (AcOH) (capture in 3M GuHCl+1% Triton, and ethanol washes). B. Measurement of the amount of nucleic acids by chromatographic analysis.
Figure 4B:
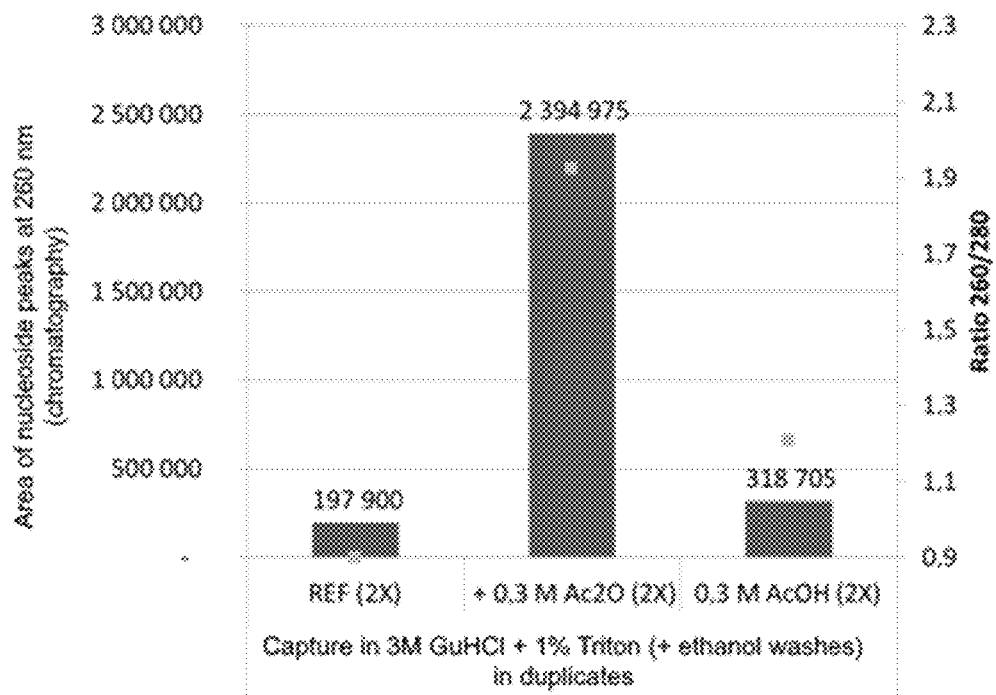

The hydrolysates were analyzed by HPLC so as not to have protein interference, and the area corresponding to the nucleosides (DNA and RNA) was measured in the chromatograms by integration of the clusters corresponding to the nucleosides. The results obtained show that the blood sample previously treated with acetic anhydride contains 12 times more nucleic acids than the untreated sample or the sample treated with acetic acid (which is non-acylating) (FIG. 4B).

Example 6: Improving the Extraction Yield of Nucleic Acids in Blood (Extraction with Silica-Based Magnetic Particles at pH 5.5)

The same experiment as the one described in Example 5 was carried out, but with changing the extraction conditions for the nucleic acids (different buffer solutions).

To 133 μL of a blood solution are added 237 μL lysis buffer (6M GuHCl, 15% Triton, AcONa, pH 5.5) and 6 μL, 12 μL, or 24 μL Ac$_2$O. The medium is incubated while stirring for 3 to 5 min in the thermomixer at 25° C. and 500 rpm, before adjusting the pH to 5.5 if necessary by adding a few p.1 of 10M NaOH. For example, 3 μL, 4.5 and 6.8 μL NaOH are added for 6 μL, 12 μL, and 24 μL Ac2O respectively. The lysate is added to the magnetic silica particles in order to extract the nucleic acids. Wash solutions (3 times 70 μl Wash Buffer IX) precede the elution step which takes place in a solution of 70 μl Tris HCl while stirring at 1400 rpm, at 70° C. for 5 minutes. The lysates are subjected to the action of the hydrolysis enzymes of the nucleic acids as described in Example 5, in order to determine the amount of nucleic acids extracted. The obtained results show that the addition of the masking reagent (acetic anhydride) in the presence of blood makes it possible to double the amount of nucleic acids extracted.

An optimum is observed under these conditions at around 6 μl pure acetic anhydride. At this concentration and in the presence of 15% Triton in the lysis buffer, the amount of nucleic acid eluted is doubled overall. The ratio rA/(rA+dA) shows that RNA is predominantly present in the eluate at 70% compared to 10% on the nanoparticle, indicating that it is preferentially eluted.

Example 7: Treatment of DNA with Acetic Anhydride Under the Conditions of the Method According to the Present Disclosure Does Not Alter the Chemical Structure of the Nucleosides In order to demonstrate the reaction selectivity of acetic anhydride towards nucleic acids, the inventors carried out the following experiment:

After incubating for 10 min a mixture of 92 mg DNA in 360 µl of 3.3M GuHCl, 50 mM Tris HCl pH 7 in the presence of 0.6M acetic anhydride (24 µl), the DNA was purified by an ultrafiltration unit (Ultracel YM-50) to eliminate the acetic anhydride which is partially UV-absorbent. This sample was then subjected to complete lysis with a mixture of Nuclease P1 and alkaline phosphatase before being analyzed by HPLC (Conditions A). The obtained results show that the DNA hydrolyzate has exactly the same profile, whether or not acetic anhydride is present. Only the expected nucleosides are detected, and no acylated nucleosides. A search for acylated nucleosides by mass spectrometry was also performed without finding these products. These results show that the acylation reaction with acetic anhydride is indeed selective and does not affect the extracted nucleic acids.

Figure 5:
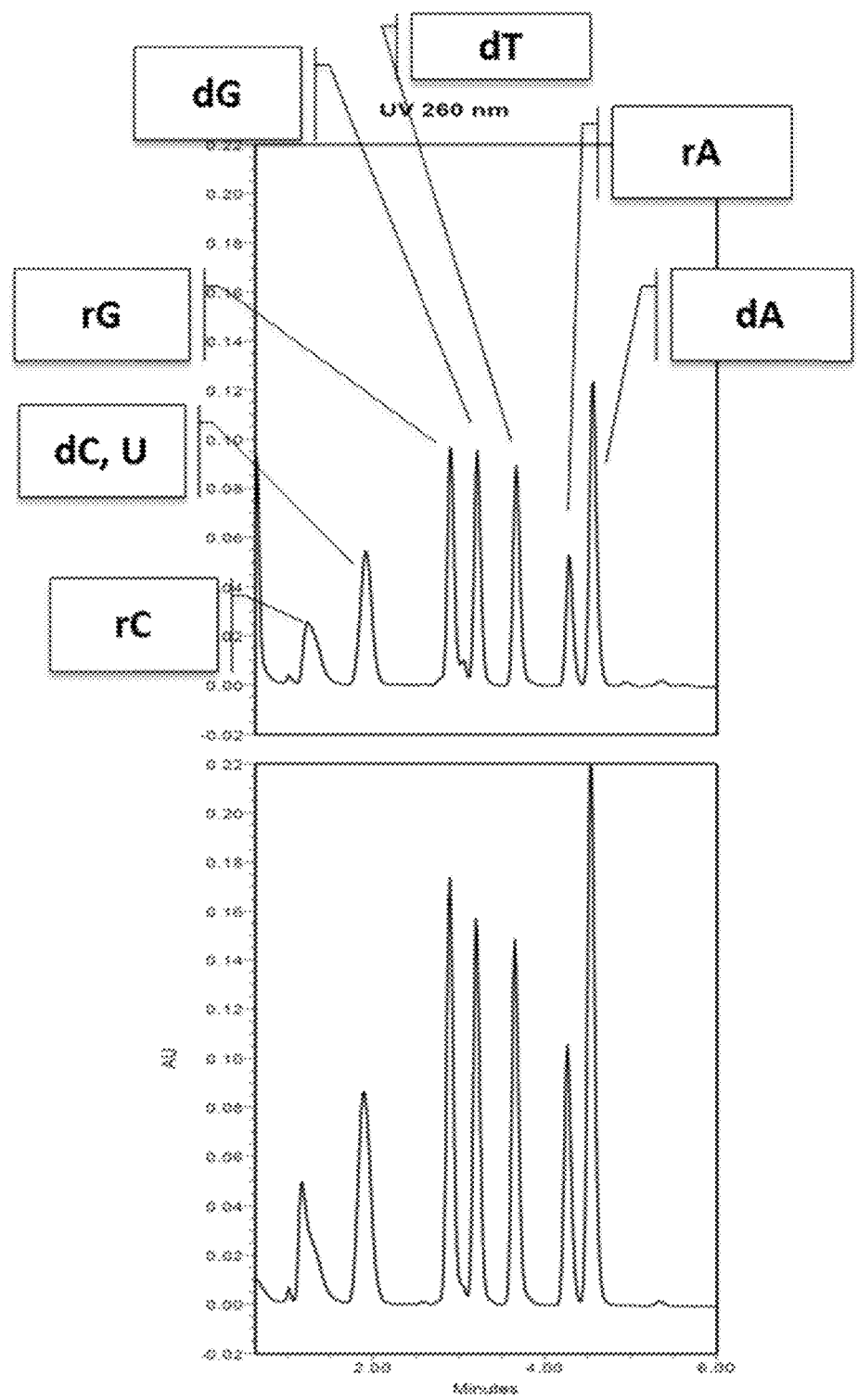
FIG. 5: HPLC analysis of extraction eluates of a mixture of DNA and RNA that is or is not subjected to acetic anhydride. Top: Eluate obtained from extraction of a mixture of 10 μg DNA and RNA and 5.2 mg proteins in the presence of acetic anhydride. Bottom: Eluate obtained from extraction of a mixture of 10 μg DNA and RNA.

Example 8: Demonstration that the Structure of DNA and RNA is Not Affected During Treatment with Acetic Anhydride Under Nucleic Acid Extraction Conditions The same demonstration as in Example 7 was carried out, this time using a mixture of DNA and RNA which are placed in the presence or absence of acetic anhydride and then extracted with magnetic silica particles. Enzymatic hydrolysis of these eluates unambiguously confirmed that there are no chemical modifications of the nucleosides after the action of acetic anhydride (see FIG. 5). It can therefore be concluded that the nucleic acids thus extracted should be amplifiable by PCR or by any other reaction for the enzymatic amplification of genetic material.

Example 9: Acetic Anhydride Treatment of a Blood Sample Makes it Possible to Detect CMV Virus with More Sensitivity A 200 µl sample of blood containing CMV virus (Cytomegalovirus in culture) to the amount of 10e4 copies is added to 800 µl lysis buffer (6M GuHCl, 15% Triton, AcONa, pH 5.5) to which 9 ml pure acetic anhydride, and optionally 1 µl of 10M NaOH, are added after a few minutes of reaction.

A control is created with blood where there is no prior treatment with acetic anhydride, and another with no blood sample, corresponding to 63 µl Tris HCL pH7 containing 10e4 copies of CMV then mixed with 237 µl lysis buffer.

The nucleic acids contained in the lysate are then extracted and purified as described in Example 6. The eluate is then subjected to real-time PCR amplification using an RGene CMV kit (kit CMV 69-003B: lot 1005408010, BioMérieux, Marcy-L'Étoile, France) and a thermal cycler (CFX96 Touch™ BioRad) to allow determining the detection sensitivity for the extracted nucleic acids, expressed in number of PCR cycles (Ct). This number is a function of the concentration of nucleic acids: the lower it is the easier it is to detect the nucleic acids of the pathogen because the initial concentration of nucleic acids is high. There is a scaling factor of 10 between each Ct (logarithmic scale).

Figure 6:
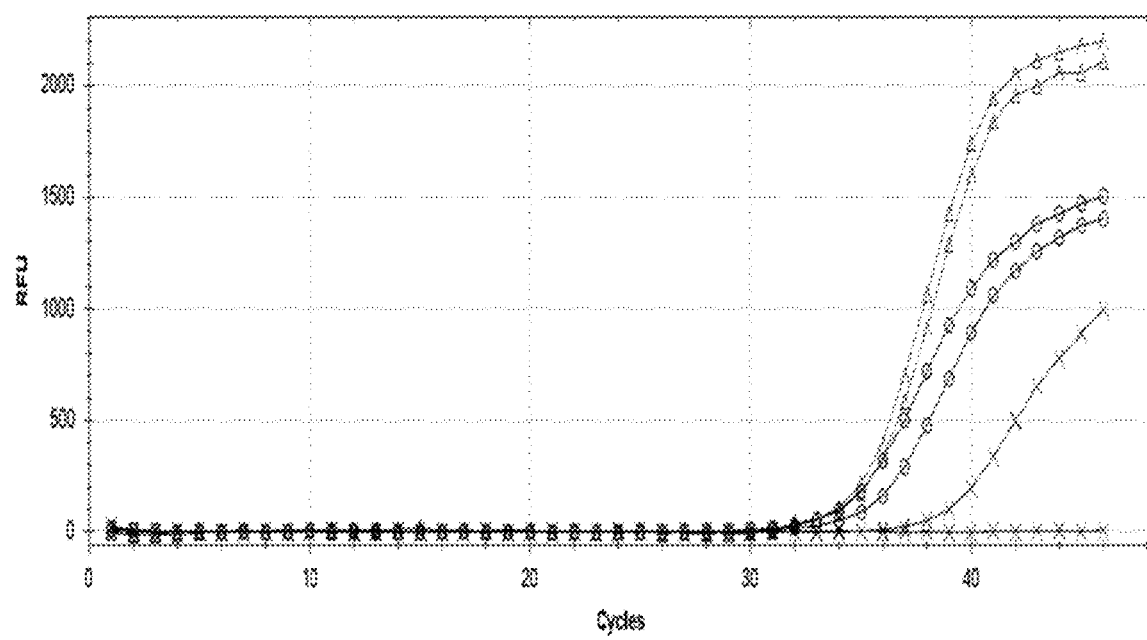
FIG. 6: Curve of fluorescence detection (RFU) of the amplification in real time of CMV virus nucleic acids in blood by PCR. The curves of FIG. 6 respectively correspond to the control amplification carried out after extraction without a biological matrix (triangles), with a biological matrix without treatment by acetic anhydride (X shapes), and with a biological matrix with treatment by acetic anhydride (circles).

The curves of FIG. 6 respectively correspond to the control amplification carried out after extraction with no biological matrix (triangles), with a biological matrix without treatment by acetic anhydride (X shapes), and with a biological matrix with treatment by acetic anhydride (circles). The number of PCR cycles is therefore at 34 Ct when the CMV virus has been extracted without a biological matrix, then rises to 38 Ct when the same amount of nucleic acids is extracted from a sample containing blood. This shows that the inhibitors contained in the biological matrix are responsible for the loss of more than 99.9% of the initial nucleic acids. The Ct number returns to 34 which is equivalent to a sample without matrix when the sample is previously treated with acetic anhydride. These data show a remarkable improvement in the detection sensitivity in the presence of a biological matrix.

Figure 7:
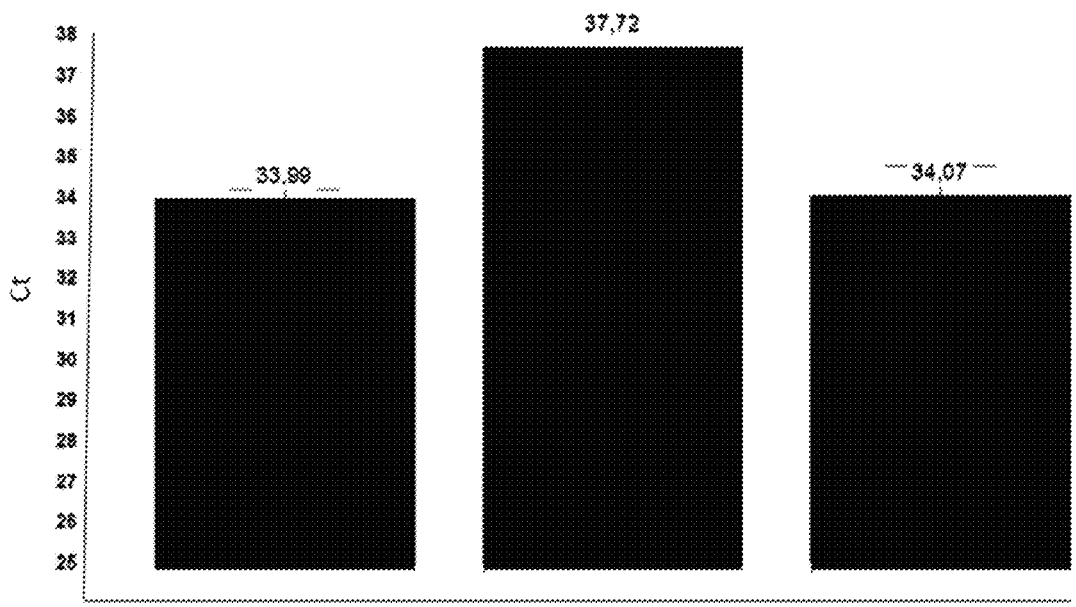
FIG. 7: Sensitivity of the detection of CMV virus in blood, without or with treatment with acetic anhydride Ac2O prior to extraction (Ct): Left: 10e4 copies of CMV in Tris HCl; Center: 10e4 copies of CMV in blood; Right: 10e4 copies of CMV in blood+Ac2O.

FIG. 7 is another representation of FIG. 6, with further clarification of the Ct.

Example 10: Improving the Extraction of Nucleic Acids in the Presence of a High Protein Concentration by Using Acetic Anhydride (Use of an Extraction Column with Silica Membrane)

In this example, the inventors have used a nucleic acid extraction medium that is different from magnetic silica particles, in order to demonstrate that acetic anhydride is also of interest in other extraction technologies such as extraction columns with silica membrane.

10 µg salmon sperm DNA (20 kB) are mixed in 300 µl of a solution of 3M GuHCl, 50 mM AcO—Na pH 5.5, and 30% ethanol with increasing concentrations of a mixture of hemoglobin and human serum albumin at levels of 0.300, 600, 1200, 1800, and 2400 µg (with a hemoglobin/HSA ratio of 3/1).

This mixture is treated or not treated with 6 µl acetic anhydride for a few minutes (10) while stirring in the thermomixer.

The mixture is neutralized with 1 µl of 5M NaOH to restore the pH to 5.5.

The mixture is deposited on a QiaQuick column (Qiagen, Heiden, Germany) and centrifuged for 6 minutes at 13,200 rpm.

The column is washed 3 times with 200 µl of 50 mM MES pH 5.5/80% ethanol while centrifuging at 13,200 rpm for 3 minutes.

The immobilized nucleic acids are then eluted with 200 µl borate buffer pH 8.5 at 3 mM for the first time, then this solution is passed through again to elute all the nucleic acids.

The eluate is subjected to enzymatic hydrolysis, then the extracted nucleic acids are quantitated by chromatographic analysis.

Figure 8:
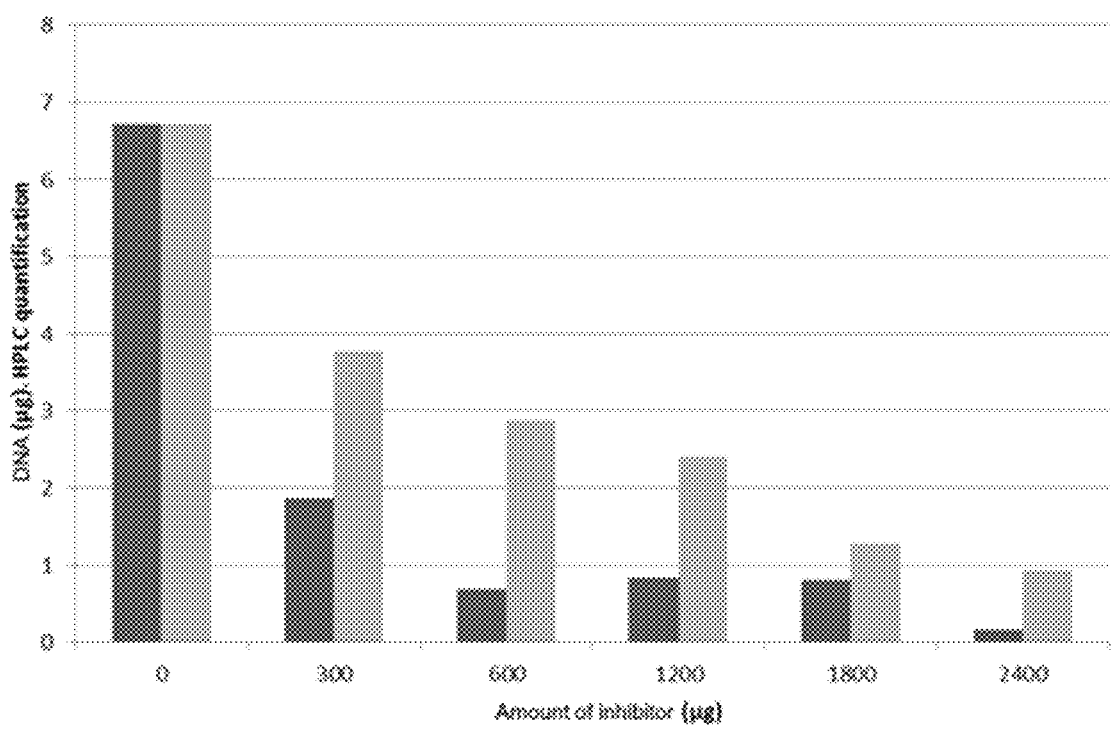
FIG. 8: Extraction of DNA in the presence of a mixture of human serum albumin and hemoglobin on a column with silica membrane, with and without treatment with Ac2O. Left (dark gray): without Ac2O treatment; Right (light gray): with Ac2O treatment

In FIG. 8, one can see a significant improvement in the amount of DNA extracted when the sample has been subjected to acetic anhydride.

Figure 9:
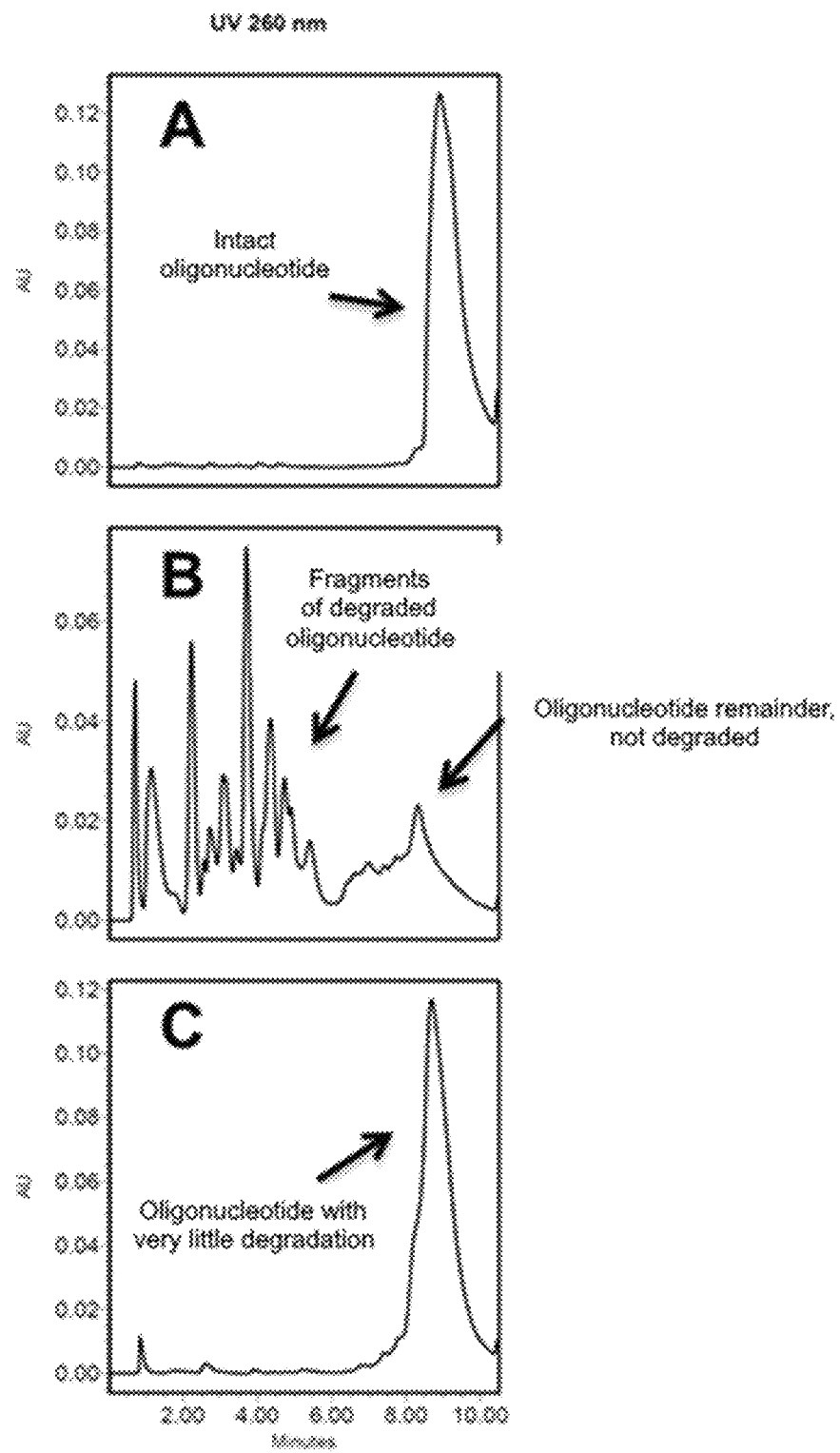
FIG. 9: Chromatogram corresponding to an intact oligonucleotide (A), the same oligonucleotide in the presence of Nuclease P1 and therefore degraded (B), and the same oligonucleotide in the presence of Nuclease P1 and acetic anhydride showing much better stability of the oligonucleotide due to acylation of the nuclease (C).

Example 11: Demonstration that the Use of Acetic Anhydride According to the Invention Also Allows the Inhibition of Nucleases A model oligonucleotide of 60 bases (1 nmol) is placed in contact with 0.01 units of nuclease P1 in 48 µl water and 48 µl of 500 mM MES pH 4.7 while adding or not adding 6 µl pure acetic anhydride. The results are shown in FIG. 9. Compared to the control oligonucleotide which has undergone no treatment (chromatogram A), in the case where there is no acetic anhydride, the oligonucleotide is immediately hydrolyzed by the nuclease (chromatogram B). On the other hand, in the case where acetic anhydride has been added, there is very little degradation of the oligonucleotide (chromatogram C). This therefore demonstrates that acetic anhydride allows inactivation of the nuclease by alkylating it.

Example 12: Demonstration that the Reagent can Selectively React with Proteins Under Chaotropic Conditions (Case of Acetic Anhydride)

Figure 10:
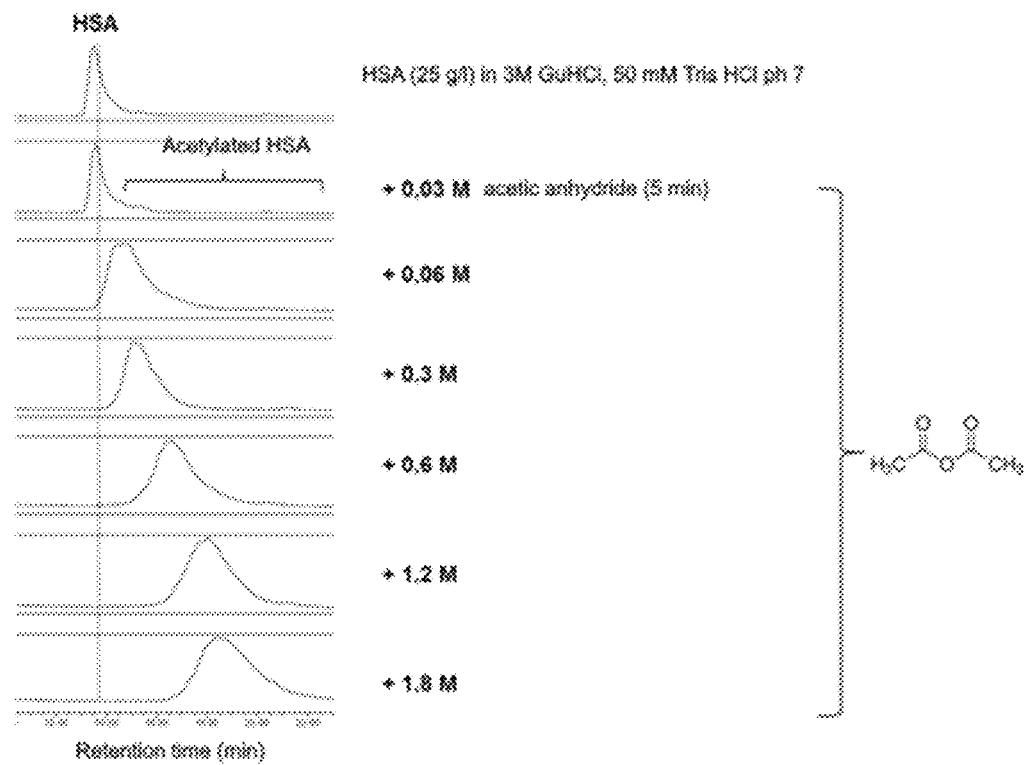
FIG. 10: HPLC monitoring of the acetylation of HSA at 25 mg/ml by between 0 and 1.8 M acetic anhydride under lysis conditions (3M GuHCl or 3M GuSCN, 50 mM Tris HCl pH 7).
Figure 11:
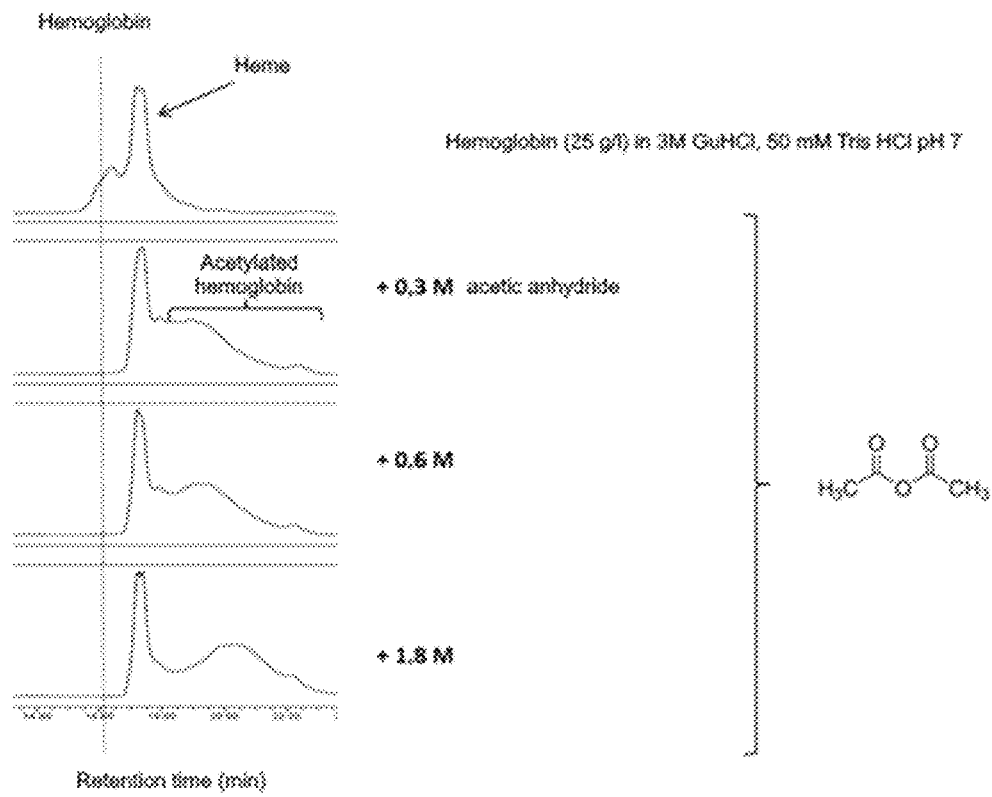
FIG. 11: HPLC monitoring of the acetylation of hemoglobin at 25 mg/ml by between 0 and 1.8 M acetic anhydride under lysis conditions (3M GuHCl, 50 mM Tris HCl pH 7).

FIGS. 10 and 11 show HPLC monitoring (Conditions B) of the acetylation of HSA or hemoglobin at 25 mg/ml by between 0 and 1.8 M acetic anhydride under lysis conditions (3M GuHCl or 3M GuSCN, 50 mM Tris HCl pH 7). One can see after 5 minutes of reaction and depending on the concentration of acetic anhydride that the cluster corresponding to the protein widens and moves to the right, indicating that the protein is becoming more hydrophobic which is the result of its acylation. In the case of HSA, when a concentration around 1.2 M is reached, the retention time no longer changes, which means that all the nucleophilic groups of the protein have reacted. In the chromatograms monitoring the hemoglobin acetylation, note that the heme is not modified by acetylation and does not undergo any change in its retention time.

It is thus shown that acetic anhydride can react rapidly and efficiently on proteins under lysis conditions and in the presence of nucleophilic compounds such as Tris.

The fact that acetic anhydride can acetylate a protein in an aqueous medium while being selective is a true surprise, since the majority of reactions with acetic anhydride are described in an organic solvent. Due to the presence of water, Tris, and guanidine which are likely to hydrolyze it, it was not obvious that acetic anhydride can react at low concentrations with a protein.

The invention claimed is:

1. A method for extracting nucleic acids from a sample comprising proteins and/or polysaccharides, said method comprising:
   a step of treating the sample with:
      a reagent for masking the amine functional groups of the proteins and/or polysaccharides of the sample, which is selected from acylating agents in concentrations between 0.1 and 1.8 M, and/or
      a reagent for masking the carboxylic acid functional groups of the proteins and/or polysaccharides of the sample, which is selected from the group consisting of amines, alcohols, and thiols, in combination with a coupling agent; and
   a step of capturing nucleic acids by placing the treated sample in contact with a suitable solid support,
   wherein the nucleic acids are not modified by the masking reagent.

2. The method according to claim 1, wherein the treatment step comprises treating the sample with the reagent for masking the amine functional groups.

3. The method according to claim 2, wherein the masking reagent is selected from acylating agents of the following formula (I):

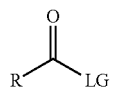 (I)

where
   R is an organyl, organyloxy, or organylamino group, and
   LG is a leaving group selected from the group consisting of halogens, organyloxy and organylamino groups.

4. The method according to claim 1, wherein the masking reagent for masking the amine functional groups is an acylating agent selected from the group consisting of activated esters, acid halides, chloroformates, anhydrides, activated carbonate esters, and carbonyldiimidazole.

5. The method according to claim 1, wherein the masking reagent for masking the amine functional groups is an anhydride selected from acetic anhydride, propionic anhydride, isobutyric anhydride, butyric anhydride, or benzoic anhydride.

6. The method according to claim 1, wherein the treatment step comprises treating the sample with the reagent for masking the carboxylic acid functional groups.

7. The method according to claim 6, wherein the coupling agent is a carbodiimide.

8. The method according to claim 1, wherein:
   the sample is a biological sample comprising cells,
   the method further comprises lysing the cells of the biological sample,
   the treatment step comprises treating the lysate with the reagent for masking the amine functional groups and/or the reagent for masking the carboxylic acid functional groups, and
   the capture step comprises capturing the nucleic acids by placing the treated lysate in contact with a suitable solid support.

9. The method according to claim 1, wherein the suitable solid support consists of silica particles.

10. The method according to claim 8, wherein the biological sample is a sample of blood, plasma, or serum.

11. The method according to claim 8, wherein the capture step is carried out in the presence of chaotropic agents.

12. The method according to claim 8, wherein the method does not comprise the use of proteases for the removal of proteins.

13. The method according to claim 8, wherein no organic solvent is added before or during the capture step.

14. The method according to claim 8, further comprising detecting nucleic acids of interest.

15. The method according to claim 8, further comprising:
   a washing step of washing the support with a wash buffer.

16. The method according to claim 15, further comprising:
   eluting the nucleic acids after the capture step or the washing step.

17. The method according to claim 9, wherein the suitable solid support consists of magnetic silica particles.

18. The method according to claim 14, wherein the detecting nucleic acids of interest is performed by amplification of the extracted nucleic acids.

19. The method according to claim 1, wherein the method does not include a step of deprotecting the masked amine functional groups and/or masked carboxylic acid functional groups.

* * * * *